(12) United States Patent
Cohn et al.

(10) Patent No.: US 11,666,474 B2
(45) Date of Patent: Jun. 6, 2023

(54) FEMALE URINARY DEVICE

(71) Applicant: TILLA CARE LTD, Tirat Carmel (IL)

(72) Inventors: Michael Cohn, Tirat Carmel (IL); Nuphar Haller, Tirat Carmel (IL); Ilan Alfia, Kiryat Ata (IL); Sana Yassin, Tirat Carmel (IL); Amir Laniado, Tirat Carmel (IL); Lora Parahovnik, Tirat Carmel (IL)

(73) Assignee: Tilla Care Ltd., Tirat Carmel (IL)

( * ) Notice: Subject to any disclaimer, the term of this patent is extended or adjusted under 35 U.S.C. 154(b) by 276 days.

(21) Appl. No.: 16/472,086

(22) PCT Filed: May 27, 2018

(86) PCT No.: PCT/IL2018/000005
§ 371 (c)(1),
(2) Date: Jun. 20, 2019

(87) PCT Pub. No.: WO2018/235065
PCT Pub. Date: Dec. 27, 2018

(65) Prior Publication Data
US 2020/0085610 A1    Mar. 19, 2020

Related U.S. Application Data

(60) Provisional application No. 62/521,694, filed on Jun. 19, 2017.

(51) Int. Cl.
*A61F 5/443*    (2006.01)
*A61F 5/455*    (2006.01)
(Continued)

(52) U.S. Cl.
CPC ............ *A61F 5/443* (2013.01); *A61F 5/4408* (2013.01); *A61F 5/451* (2013.01); *A61F 5/455* (2013.01); *A61F 5/4556* (2013.01); *A61B 10/007* (2013.01)

(58) Field of Classification Search
CPC ........ A61F 5/443; A61F 5/4556; A61F 5/451; A61F 5/455; A61F 5/4408; A61B 10/007
See application file for complete search history.

(56) References Cited

U.S. PATENT DOCUMENTS 3,722,503 A * 3/1973 Hovick .................... A61F 5/44
                                                    600/574
3,815,581 A * 6/1974 Levin .................. A61F 5/4556
                                                    600/574

(Continued)

FOREIGN PATENT DOCUMENTS

| DE | 199 15 454 A1 | 11/2000 |
| GB | 2 090 144 A | 7/1982 |
| JP | 2011-000200 A | 1/2011 |

OTHER PUBLICATIONS

GoGiri. https://go-girl.com/product/gogirl-lavender-pink/. Accessed Mar. 19, 2018.

(Continued)

*Primary Examiner* — Susan S Su
*Assistant Examiner* — Ted Yang
(74) *Attorney, Agent, or Firm* — Smith Gambrell & Russell LLP

(57) ABSTRACT

An external female urinary device includes a connecting and urine collecting component (CUCC) and a urine directing and discharging component (UDCC) configured to connect with the CUCC. The CUCC tapers from a larger orifice to a smaller orifice. The CUCC has a ring defining the larger orifice. The ring is made of a material capable of adhering to urethral orifice surrounding skin (UOSS) as well as to the inner facing surfaces of the labia minora and/or the labia majora after the CUCC is pressed against that UOSS. The ring remains adhered to the UOSS without requiring an external force for keeping the ring in contact with that skin.

20 Claims, 11 Drawing Sheets

(51) Int. Cl.
*A61F 5/44* (2006.01)
*A61F 5/451* (2006.01)
*A61B 10/00* (2006.01)

(56) References Cited

U.S. PATENT DOCUMENTS

| | | | |
|---|---|---|---|
| 4,198,979 A * | 4/1980 | Cooney | A61F 5/455 604/329 |
| 4,246,901 A | 1/1981 | Michaud | |
| 4,496,355 A * | 1/1985 | Hall | F16K 15/144 604/327 |
| 4,568,339 A * | 2/1986 | Steer | A61F 5/455 4/144.3 |
| 4,681,572 A | 7/1987 | Tokarz et al. | |
| 4,771,484 A | 9/1988 | Mozell | |
| 4,795,449 A * | 1/1989 | Schneider | A61F 5/4405 604/329 |
| 4,815,151 A | 3/1989 | Ball | |
| 4,822,347 A | 4/1989 | MacDougall | |
| 4,846,817 A * | 7/1989 | Mohr | A61F 5/455 604/329 |
| 4,986,823 A | 1/1991 | Anderson et al. | |
| 5,053,027 A * | 10/1991 | Manfredi | A61F 5/455 604/327 |
| D393,061 S | 3/1998 | Mandich et al. | |
| 5,893,176 A * | 4/1999 | Magiera | A47K 11/12 4/144.4 |
| 6,183,454 B1 | 2/2001 | Levine et al. | |
| 6,428,521 B1 | 8/2002 | Droll | |
| 6,969,380 B1 | 11/2005 | Zunker | |
| D577,435 S | 9/2008 | Ivie et al. | |
| 7,875,010 B2 | 1/2011 | Frazier et al. | |
| 8,235,956 B2 | 8/2012 | Block | |
| 8,337,477 B2 | 12/2012 | Parks et al. | |
| 8,490,220 B1 | 7/2013 | Hajek | |
| 9,101,497 B2 | 8/2015 | Tan | |
| 9,186,234 B2 | 11/2015 | Reglin | |
| D804,654 S | 12/2017 | Stephen | |
| 10,085,876 B2 | 10/2018 | Jones | |
| 2001/0037098 A1 * | 11/2001 | Snyder | A61F 5/4553 604/331 |
| 2007/0219479 A1 * | 9/2007 | Tasbas | A61F 13/28 604/12 |
| 2007/0293937 A1 * | 12/2007 | Biggs | A61L 27/34 623/1.13 |
| 2011/0028922 A1 * | 2/2011 | Kay | A61F 5/4553 604/329 |
| 2011/0042258 A1 | 2/2011 | Nett | |
| 2011/0172620 A1 | 7/2011 | Khambatta | |
| 2015/0073370 A1 * | 3/2015 | Noda | A61F 13/534 604/378 |
| 2015/0135423 A1 * | 5/2015 | Sharpe | A61F 5/453 4/471 |
| 2016/0030228 A1 | 2/2016 | Jones | |
| 2016/0143769 A1 | 5/2016 | Mahalingam | |
| 2017/0325788 A1 | 11/2017 | Ealovega et al. | |

OTHER PUBLICATIONS

SheWee. https://www.amazon.in/Shewee-Extreme-Reusable-Female-Urination/dp/B00OHRIL0I. Accessed Mar. 19, 2018.
NASA Life Sciences Data Archive, Urine Collection Device (UCD) Hardware Information. https://lsda.jsc.nasa.gov/Hardware/hardw/764. Accessed May 2, 2019.

\* cited by examiner

FEMALE URINARY DEVICE

TECHNICAL FIELD

The subject matter described herein relates to an external female urinary device that is made of a material capable of adhering to skin surrounding urethral orifice after the urinary device is pressed against that skin, and that remains adhered to that skin without requiring an external force for keeping the female urinary device in contact with such skin.

BACKGROUND

In several parts of the world, the places where females can urinate are unsanitary and/or exposed. In such conditions, females often find it difficult to urinate while minimally exposing their nakedness to the surrounding environment. Some other females have, regardless of the location of urination, problems such as being bedridden or a condition that discourages mobility. Such females often cannot urinate without the urine leaking and wetting the surroundings, thereby causing immense physical and mental discomfort to them.

Some of the conventional urinary devices fail to help females, such as those noted above. For example, the traditional urinary devices: leak urine; do not work for extended durations of time; do not work for changing physiological conditions induced by the movement of the body of the female; need external forces—e.g., hands of a female, belts, straps, stabilizers, support panels, plates, adhesives, other external apparatuses, and/or the like—to remain within the body of the female; do not easily connect to or disconnect from the body of the female; have an uncomfortable structure that is not ergonomic and often induces discomfort to the female; are difficult to deploy within the female; and cause discomfort and skin irritation to the user, especially when the urinary device is in use for extended time durations.

There accordingly exists a need for a female urinary device that addresses at least the above-presented problems of the conventional urinary devices.

SUMMARY

The subject matter described herein relates to an external female urinary device constructed of a connecting and urine collecting component (CUCC)), and a urine directing and discharging component (UDDC)) configured to connect with the CUCC. The CUCC tapers from a larger orifice to a smaller orifice. The CUCC has a ring defining the larger orifice. The surface area of the CUCC is made of a material capable of adhering to skin in the vicinity of the, inner facing surfaces of the labia minora and/or the labia majora as well as to the urethral orifice surrounding skin (UOSS) after the CUCC is pressed against the UOSS. The CUCC remains adhered to the UOSS and/or labia without requiring an external force for keeping the CUCC in contact with that skin.

In addition to the adhesion force, the CUCC of the urinary device connects to the UOSS and/or the labia by a closing-in force exerted on the CUCC. The additional closing-in force is the force exerted by the squeezing of the walls surrounding against the inserted CUCC into the space between the UOSS and the labia. The closing-in force includes the force exerted by the folding-in of the labia majora and/or labia minora towards the inserted CUCC, if and when the labia majora and/or labia minora are so developed as to engulf the CUCC.

In one aspect of the urine collection device the device is composed of: a CUCC and a UDDC. The CUCC is constructed of a crescent hollow curve-shaped funnel tapering from a larger orifice to a smaller open orifice. The CUCC has a ring defining the larger orifice. The tween the UOSS CUCC of the urine collection device is made of a material which adheres to the urethral orifice surrounding skin (UOSS) of a female after the inner wall of the hollow crescent funnel of the CUCC is pressed against the UOSS. After an adhesion is formed, the ring remains adhered to the UOSS without requiring an external force for keeping the ring in contact with the UOSS. The UDDC component is constructed in a tube configuration and is connected with the CUCC, forming a continues duct for urine passage from the CUCC to the UDDC and to a urine receptacle vessel.

In another aspect of the urine collection device, the inner wall of the hollow curve-shaped funnel adheres to the UOSS after CUCC is pressed against the UOSS and remains adhered to the UOSS without requiring an external force for keeping the ring in contact with the UOSS.

In another aspect of the urinary collection device, the CUCC and the UDDC retain their spatial configuration when the urine collection device adheres to the UOSS.

In some variations, one or more of the following aspects can be implemented either individually or in any suitable combination.

In another aspect of the urine collection device, the CUCC and the UDDC retain their shapes when the urine collection device adheres to the UOSS.

In an aspect of the connecting of the urine collecting device to the genitalia of a female, the device is constructed of both the CUCC and the UDDC, as was previously described, yet the external wall of CUCC adheres to the inner wall of a the labia (minora and majora) of a female after the CUCC is pressed against the urethral orifice surrounding skin (UOSS), the CUCC remaining adhered to the labia without requiring an external force for keeping the CUCC in contact with the skin of the labia, In another aspect of the urine collection device, the CUCC and the UDDC retain their shapes when the urine collection device adheres to the labia.

In another aspect of the urine collection device, the device is made of a viscoelastic, biocompatible silicone based material having smooth surfaces that bestow an adhesion skin-device force that enables the ring of the CUCC to remain adhered to the UOSS and/or the labia.

In another aspect of the urine collection device, the urine collection device is constructed so that the CUCC and the UDDC have a single entity configuration.

In another aspect of the urine collection device, the ring of the CUCC of has a substantially flat plate-structure perpendicularly connected to the edge of the wall of dome-like funnel, forming a T-shape at the edge of the larger orifice.

In another aspect of the urine collection device the hollow curve-shaped funnel has a dome-shaped structure.

In another aspect of the urine collection device a skirt-like structure is connected to and surrounds the CUCC.

In another aspect of the urine collection device has a wing attached to the CUCC.

In another aspect of the urine collection device, the device has a wing attached to the UDDC.

In another aspect of the urine collection device the wing mentioned above is constructed of a plurality of bars.

In another aspect of the urine collection device, the mentioned plurality of bars of the wing are in a parallel configuration.

In another aspect of the urine collection device, the above mentioned wing is has on it a plurality of bumps.

In another aspect of the urine collection device the CUCC is configured to be placed in entirety in a space between the inner surface of the labia and the UOSS.

BRIEF DESCRIPTION OF DRAWINGS

Like reference symbols in the various drawings indicate like elements.

DETAILED DESCRIPTION

Figure 1:
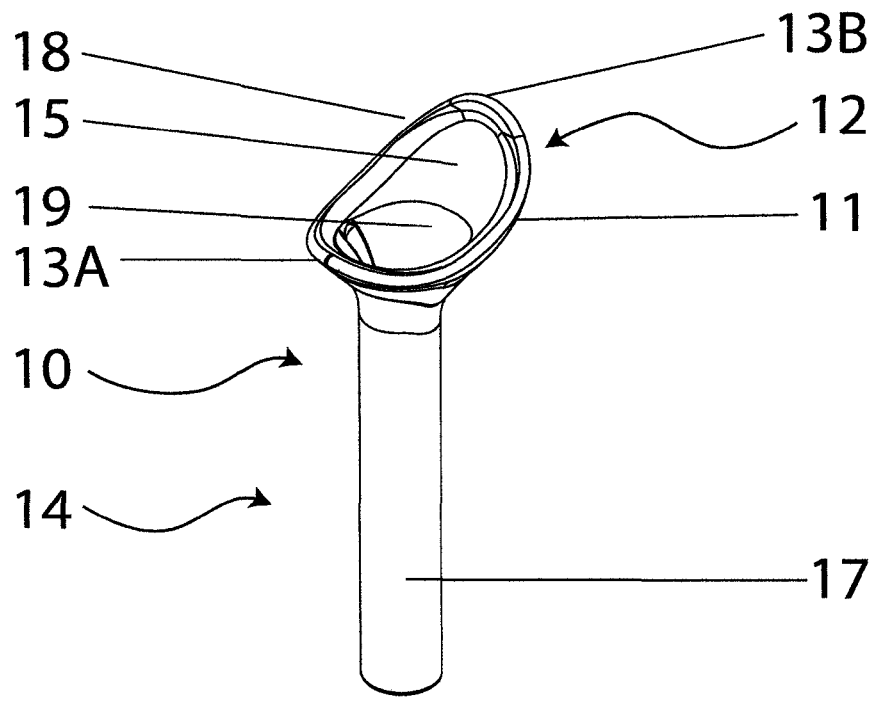
FIG. 1 illustrates a top perspective view of a first embodiment of a female urinary device.

The term "contact" can refer to a physical connection between surfaces in a fixated configuration. The term "stabilize" can refer to maintaining of contacted surfaces in a steady configurational state. The term "genitalia" can refer to the labia majora and/or labia minora as well as the perineum skin of the tissue surrounding the urethra orifice and the vagina orifice and does not include the clitoris. The female urinary device is placed adjacent to and connected to the genitalia of the user. The term "urethral orifice surrounding skin" (abbreviated as UOSS) is defined as the perineum skin of the tissue surrounding the urethra orifice as well as the skin tissue surrounding the vaginal orifice and not including the clitoris. The female urinary device is also referred to herein as a urine collection device, a urinary device, a urine device, a device, or the like.

To connect the urinary device to the genitalia, the CUCC is entirely inserted into the space between the labia majora and/or labia minora and the UOSS. The inserted component reversibly connects to the UOSS and to the surfaces of the inward facing surfaces of the labia majora and/or labia. Two factors play a role in the connection; (I) an adhesion force between contacting surfaces, and (II) a squeezing mechanical force, exerted by the walls surrounding the inserted CUCC from both sides below the labia minora "wanting" to return to the upstretched state In addition, on contact of the CUCC with the UOSS the UOSS is minorly stretched. The force exerted by the USOSS "wanting" to return to the upstretched state stabilizes the device in place. If the labia majora and/or labia minora are well developed, their folding in towards the body adds to the mechanical force exerted by the walls squeezing. The mechanical force is referred to as the: "closing-in force,".

The stabilizing of the connection of the urinary device (but not part taking in the connection) is obtained by the insertion of a small portion of the urinary device into the vaginal orifice, as explained later on in the text.

The terms "frontal" and "back" side of the urinary device refers to the side of the urinary device aligned with the body direction of the user, meaning the forward facing side and the rear side of the user of the urinary device. In the embodiments described below, the "upside" of the urinary device refers to the side of the urinary device that connects to the body of the user, and the "downside" refers to the opposite side of the urinary device.

Human skin is in general a low surface energy surface, it is primarily hydrophobic and has a low surface tension of 25-29 dyne/cm. To be biocompatible (to form a stable connection) the surface coming into contact with the skin should have an equivalent or lower surface tension. Silicone polymers and PTFE (Polytetrafluoroethylene) substances typically have a surface tension on 18 and 21 dyne/cm, respectively, thus, will generate a "sticking phenomena" when coming in contact with the skin. The "sticking phenomena" will of course be true for any biocompatible substance having the same surface tension of 18 and 21 dyne/cm. Thermoplastic elastomers (TPE, and which can also be referred to as thermoplastic rubbers) includes several types of compounds that typically have a surface tension energies in the range of 30-45 dyne/cm, thus, not suited for the urinary device. A very thin biocompatible liquid film between the skin and a surface of a low surface-tension material substantially increase the sticking phenomena, referred to as an adhesion phenomena.

The urinary device can be made of biocompatible, medical grade, material(s), typically made from, but not restricted to a viscoelastic, semi rigid silicone based material.

Silicone based materials, have the ability to connect to the UOSS in a reversible yet leak-free manner by adhesion without the use of any stabilizers or adhesives. The efficacy of the adhesion, which was unexpected, is believed to be due to the chemical compatibility of the materials forming the urinary device and the smoothness/roughness and elasticity and resilience/rigidness of the contacted surfaces. Enhancing the adhesion, is the presence of intervening thin liquid film(s) between the skin and the urinary device. Often the skin of the UOSS and the inward facing of the surfaces of the labia majora and/or labia minora is naturally moist from sweat, traces of urine and vaginal excretes. If the moisture of the skin is not sufficient to form a desired film to form and enhance adhesion, the moisture of the skin is easily enhanced by smearing on the skin a small amount of water or/and biocompatible wetting-agent (but not limited) such as a glycerin/water solution. The wetting is done by means such as whipping with a wet tissue or spraying using a spraying device. The surface of the smooth surface ring of the funnel of UOSS connecting and urine collecting component (CUCC) as well as the smooth surface of the internal side of the curved dome below the ring (to be explained later in the text) of the CUCC bestows adhesion forces that are more than the required threshold value to enable the ring and the surface below the ring to remain adhered to the UOSS. CUCC can also be referred to as first component, and UDDC can also be referred to as second component.

The female urinary device can be used for females of any age, including children. The physical-size of the urinary device used depends on the structure of the body of the user. The physical-size of the urinary device used needs to fit into and fill the space between the labia majora and labia minora around the UOSS. The physical-size of a specific urinary device can accommodate a group of females having a large range of different body-size found within the full range of body sizes of females (including children), without the need to create a urinary device based on each female's individual anatomy. For various female body-size groups (such as skinny, obese or small body-size), a specific and appropriate size of the urinary device is produced. The female urinary device can be used for all females regardless of body size.

The urinary device is ergonomically designed to fit into the space between the labia majora and labia minora and the UOSS without causing discomfort. In addition, the user of the urinary device does not need any additional interfering components in connecting and maintaining the connection to the body, thus preventing uncomfortable adjustments and handling. Once the urinary device is connected to the UOSS and the labia majora and/or labia minora, it can be left connected for long time durations without further intervention and without urine leaks that may lead to the development of microbiological caused skin infections and urine chemical-contact skin irritations in the vicinity of the genitalia. The prevention of leaks also eliminates the stench caused by ambient exposed urine.

The urinary device can be used for immediate and short-time use (connected, used and removed soon after use) as well for long duration use, meaning left connected for several hours or several days at a time. To prevent the development of infections during long duration use, the urinary device can be disconnected, the connecting surfaces of the urinary device and body of user disinfected (by wiping, using medical disinfecting liquid solution) and the urinary device reconnected to the body of the user. The disinfecting procedure can be done in a matter of a few minutes.

The urinary device is composed of two components: (I) a connecting and urine collecting component (CUCC), and (II) a urine directing and discharging component (UDDC). Optionally, two components can be manufactured as a single entity structure.

The CUCC is typically structured as an elongated, crescent-shaped, hollow and shallow concaved dome-shaped funnel, having a larger opened-top orifice and smaller open-bottom orifice and smooth inner and external surfaces. The opened-top orifice has an approximately elliptical shape smooth margin ring in the circumference of its upside. The CUCC has soft, smooth texture surfaces.

The UDDC is typically composed of a hollow, smooth tube that connects to the CUCC, forming a continues duct for urine passage from the CUCC to a urine receptacle vessel.

The urinary device is preferably (but not necessarily) composed as a single entity structure, composed of the two integrated components: the CUCC and the UDDC. Optionally, the urinary device may be composed of separate CUCC and UDDC components integrally connected.

The CUCC is composed of a semi rigid material, typically a viscoelastic, semi rigid silicone based material.

In deploying the urinary device, the urinary device is typically inserted and connected to the UOSS of the user in the following manner:

Stage1: separating the two sides of the labia majora and labia minora. Stage 2: the receptacle vessel CUCC is inserted into the space between the UOSS and the internal side of the labia minora. In stage 3: release of the labia, majora and labia minora, which close around the CUCC which presses the upper side of the urinary device towards the UOSS. The margin ring and the smooth inner-surface area of the CUCC connect to the UOSS by both adhesion and the mechanical force exerted by "the closing-in" of the labia majora and labia minora.

The volume of the CUCC so designed so as to tightly fill the space between the UOSS and the labia majora and labia minora, stabilizing the urinary device.

The urinary device reversibly connects and stabilizes the genitalia by two factors, referred to as "driving forces": (I) the force applied on the CUCC by the walls surrounding the inserted CUCC as well as by the force of the folding in of the labia majora and labia minora, if and when the labia are developed (II) by adhesion of the margin ring and the smooth inner-surface area of the CUCC to the smooth surface of the UOSS. By the insertion of the protruding backside portion of CUCC into the upper potion (the rim) of the orifice of the vagina the urinary device is guided to the be in a precise positioned over the urethral orifice in the UOSS. The insertion of the device to the upper portion (the rim) of the orifice of the vagina aids in the stabilizing the device in place. In some cases the smooth inner surfaces of the labia majora and labia minora, which press on the CUCC (driving force II), contribute to the adhesion (driving force (I) by forming an adhesion connection with the external smooth surface of CUCC.

The degree of contribution of each of the mentioned "driving forces" to the connection and stabilization the urinary device in the genitalia varies and is different from female to female and changes in individual female in accordance to the to the motions and posture of the female using the urinary device.

Additional embodiments of the urinary device have integrated components added to the previously described CUCC and UDDC. Without attempting to list all possible embodiments of the urinary device, embodiments with added components are as follows: (I) surrounding the CUCC is a flexible, resilient, foldable and bendable skirt like sheet-texture structure that enhances the connection of the urinary device to the genitalia of the user, by increasing the connecting surface area (as well as the volume) of the urinary device; and (II) connected to the sides of the UDDC or the UDDC are loose, sheet-texture, resilient, flexible wing like structures either smooth or grooved that (also) increase the connecting surface area (as well as the volume) of the urinary device with the body of the user.

To further increase the contact surface area of the urinary device, the elliptical shaped margin ring in the circumference of the CUCC has a T-configuration structure made of the same material the CUCC is made of. The T-configuration structure has a smooth and soft upper rim that enables an enhanced, tight surface connection of the urine receiving receptacle vessel to the UOSS.

Four embodiments of the a female urinary device are presently described.

Embodiment number 1, urinary device (10), is shown in FIGS. 1-6.

Figure 2:
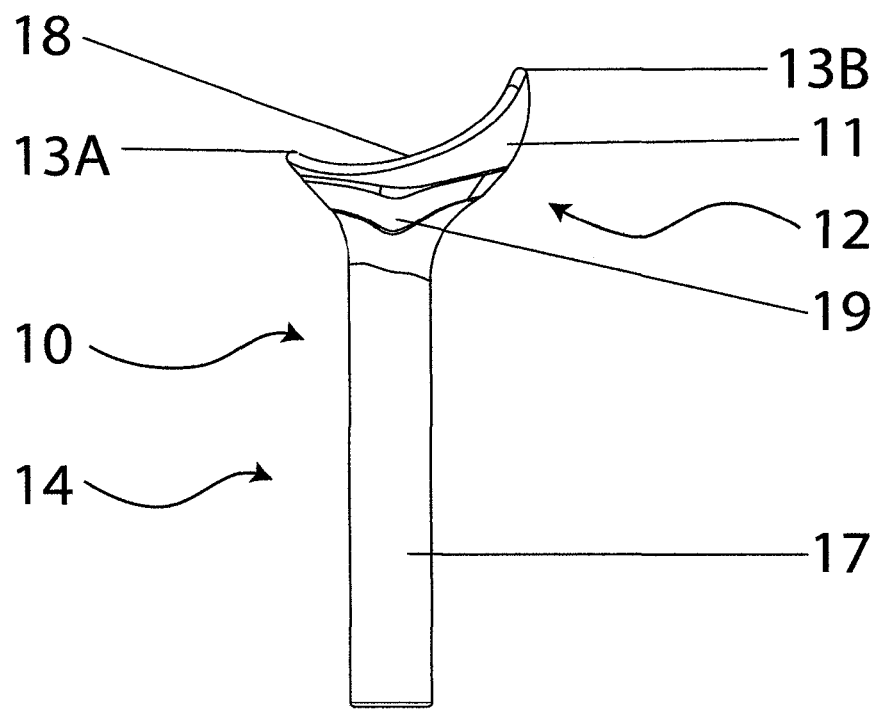
FIG. 2 illustrates a side view of the female urinary device shown in FIG. 1.
Figure 3:
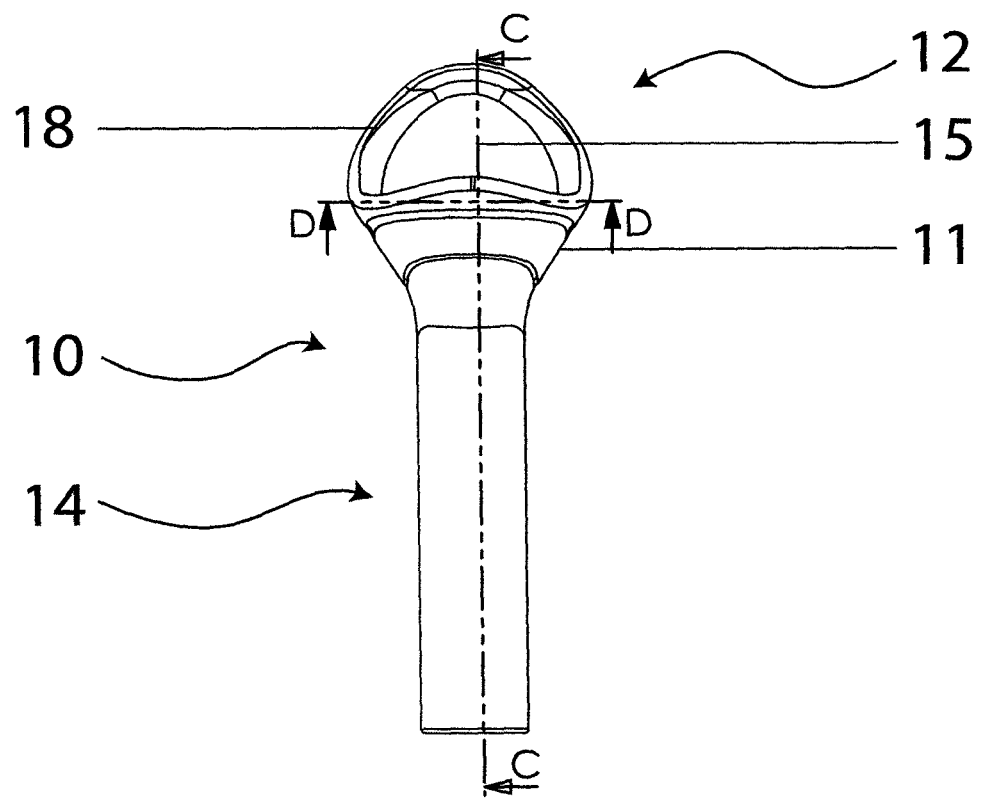
FIG. 3 illustrates a front view of the female urinary device shown in FIG. 1.
Figure 4:
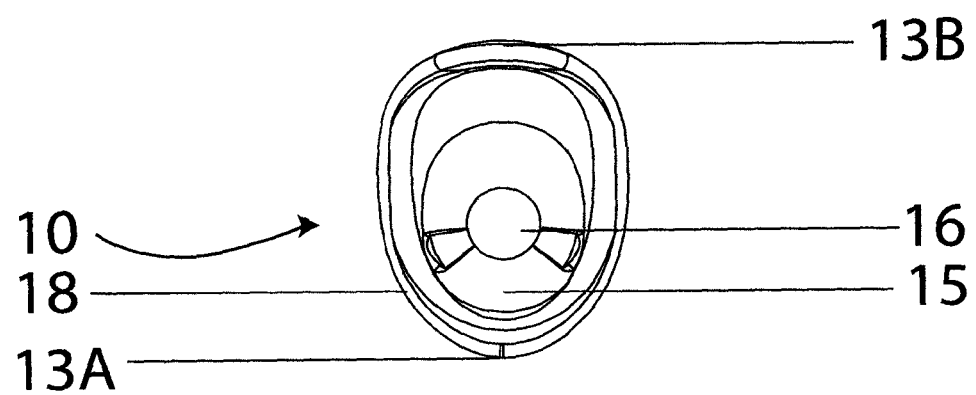
FIG. 4 illustrates a top view of the female urinary device shown in FIG. 1.
Figure 5:
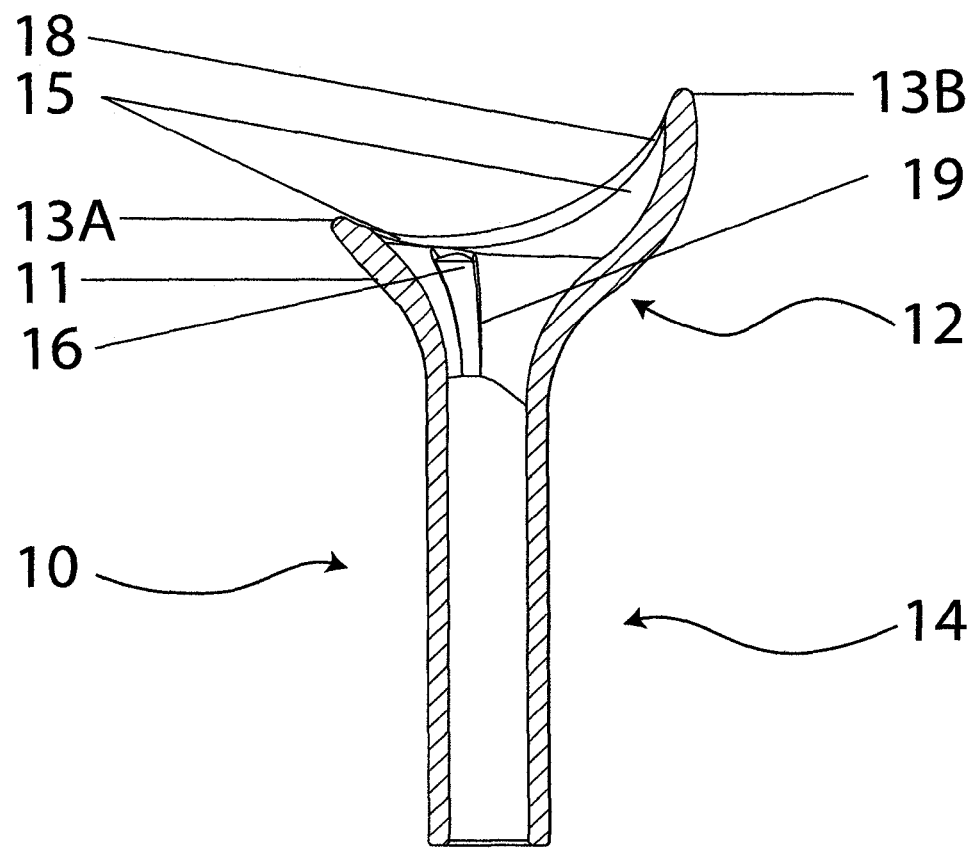
FIG. 5 illustrates a view along cross-section C-C shown in FIG. 3.
Figure 6:
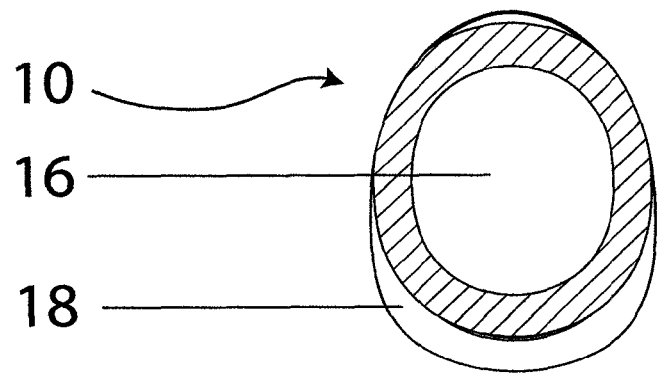
FIG. 6 illustrates a view along cross-section D-D shown in FIG. 3.

FIG. 1 illustrates the upside of urinary device (10) as seen from the side and above. FIG. 2 illustrates the side of urinary device (10). FIG. 3 illustrates the frontal side of urinary device (10). FIG. 4 illustrates the upside of urinary device (10), as seen from above. FIG. 5 illustrates a view of the cross-section C-C shown in FIG. 3. FIG. 6 illustrates a view of the cross-section D-D shown in FIG. 3.

The urinary device is typically composed of a single entity structure composed of two connected components: a genitalia connecting and urine collecting component (CUCC) (12), and a urine directing and discharging component, UDDC (14). The urinary device is produced from medical-grade (bio-compatible) viscoelastic, semi-rigid and flexible material, preferably silicone based materials, and can, alternatively, be constructed of two separate (single entity each) integrated components.

The CUCC (12) is composed of an elongated, crescent shaped, concaved opened-top, urine receiving receptacle vessel (11) having smooth inner and external surfaces (15) and an approximately elliptical shaped smooth margin-ring (18) in the circumference of the crescent-shape structure. Longitudinally, urine receiving receptacle vessel (11) has two portions: a front side portion, enumerated (13A), and a backside portion, enumerated (13B). The back side portion (13B) protrudes relatively to the frontal portion (13A) as seen when the urinary device is positioned on an horizontal plain, shown in FIG. 1, FIG. 2 and FIG. 5. The smooth inner-surface (15) and the smooth margin ring (18) readily and reversibly connect with and around the margins of the soft and smooth skin of the UOSS, enumerated: (27), shown in FIG. 14 and FIG. 15A). Towards the front side portion (13A) receiving receptacle vessel (11) has in smooth inner-surface (15) a funnel structure (19) with an open hole (16, shown in FIGS. 4 and 5). Hole (16) leads to tube (17) of UDDC (14). Opening (16) in funnel-structure (19) is located at a distance typically a quarter of the longitudinal distance between the frontal side and backside of CUCC (14).

UDDC (14) is composed of a hollow, smooth tube (17) that connects to funnel structure (19) of CUCC (12), forming a continues hollow tube for the passage of urine from funnel (19), opening hole (16) leading to through tube (17) in UDDC (14) to the outer surrounding. The open-end of tube (17) connects to a tube that drains the urine from the urine receiving receptacle vessel (11) to a urine receptible vessel, typically, a disposable plastic collection bag.

Figure 7:
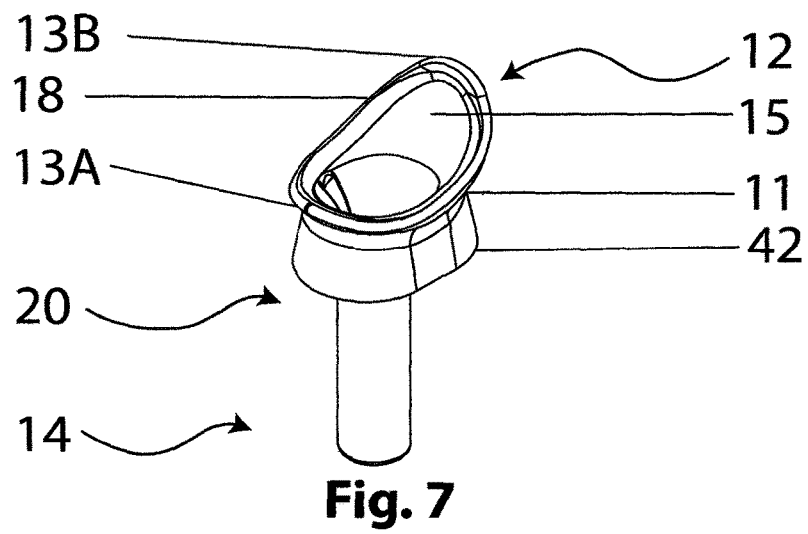
FIG. 7 illustrates a top perspective view of a second embodiment of the female urinary device.
Figure 8:
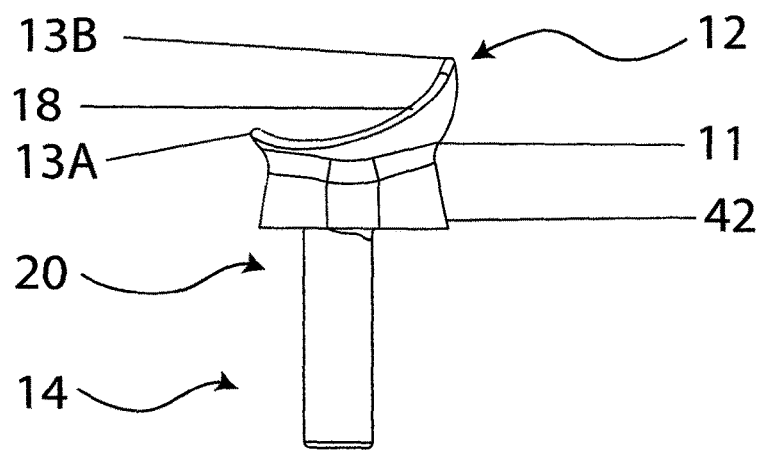
FIG. 8 illustrates a side view of the female urinary device shown in FIG. 7.
Figure 9:
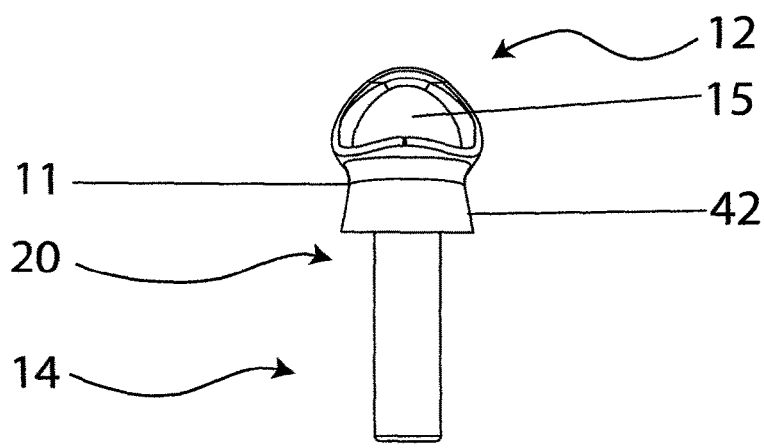
FIG. 9 illustrates a front view of the female urinary device shown in FIG. 7.

A second embodiment, urinary device (20), is shown in FIGS. 7-9. In this embodiment, CUCC (12) has surrounding it a skirt-like like structure (42) composed of a smooth and soft flexible and resilient sheet of the same material CUCC (12) is made of. Structure (42) is an integral part of the urinary device and typically connects to approximately middle of the CUCC (12) and typically reaches and surrounds upper portion of UDDC (14).

FIG. 7 illustrates urinary device (20) showing the upside of the urinary device, as seen from the side and above. FIG. 9 illustrates the side of urinary device (20), shown in FIG. 7. FIG. 9 illustrates the front side of urinary device (20), shown in FIG. 7.

Figure 10:
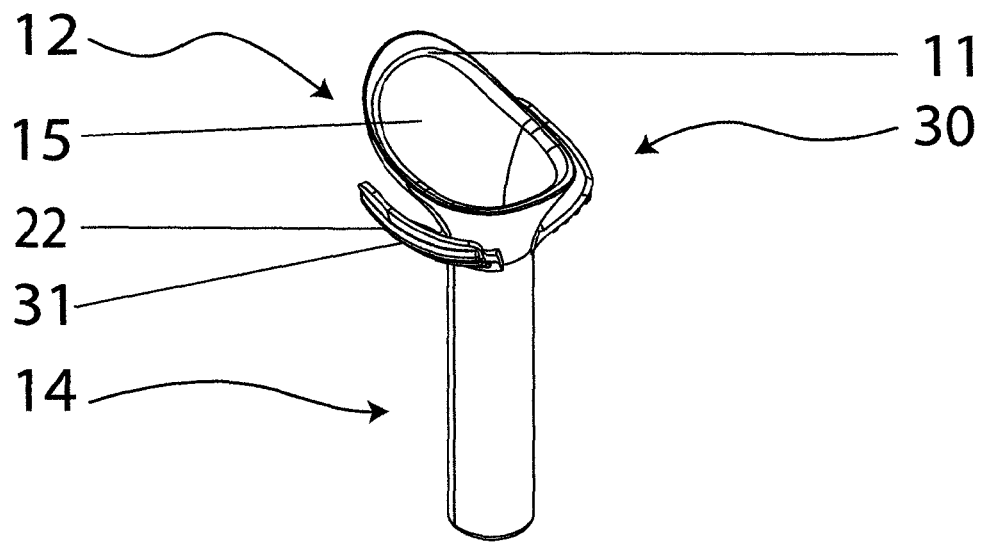
FIG. 10 illustrates a top perspective view of a third embodiment of the female urinary device.

In another embodiment, urinary device (30), shown in FIG. 10, at least two loose smooth, flexible, resilient and soft wing like structures sheets (22) connect at, or close to, the location of connection of UDDC (14) and CUCC (12) and protrude towards the upper side of the urinary device, not reaching the rim of the CUCC. Sheets (22) typically have on their side facing away from the bump-shape structures and/or bar structures (31 and 33 shown in FIG. 11) protruding from the sheets (22).

FIG. 10 illustrates urinary device (30) showing the upside of the urinary device, as seen from the side and above.

Figure 11:
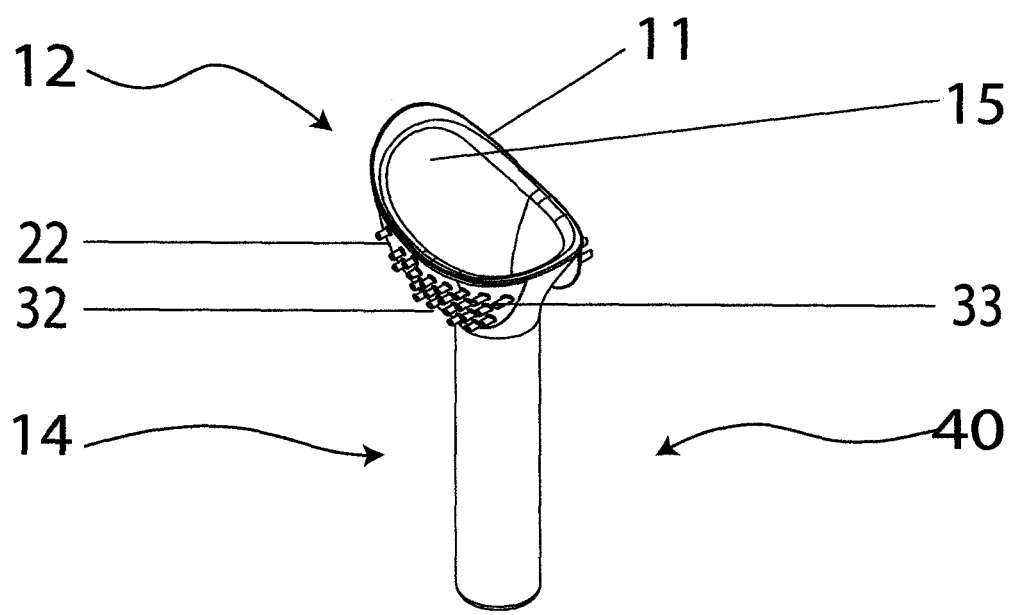
FIG. 11 illustrates a top perspective view of a fourth embodiment of the female urinary device.

In yet another embodiment, urinary device (40), shown in FIG. 11, at least two loose, smooth, flexible, resilient and soft protruding wig like structure sheets (32) connect at, or close to, the rim of CUCC (12) and protrude towards the UDDC (14), not reaching the UDDC. Sheets (32) typically have on their side facing away from the bump-shape structures and/or bar structures protruding from the sheet (33 and 31, shown in FIG. 10).

FIG. 11 illustrates urinary device (40) showing the upside of the urinary device, as seen from the side and above.

The purpose of the skirt-like like structure (42) as well as the smooth, flexible, resilient and soft wing like structure sheets ((22) and (32)) and the bump-shape structures and/or bar structures ((31) and (33)) is to increase, by bending and folding, the surface contact area between CUCC (12) and the body of the female using the urinary device, thus increasing the area of adhesion and strengthen the connection between the urinary device and the labia majora (72), the labia minora (74) and the UOSS (27) of a treated female (78). The effect of the structures (31), (32) and (42) play a more significant role in the connection of the urinary device in young females and in females, where the labia majora (72) and the labia minora (74) are relatively undeveloped.

Figure 12A:
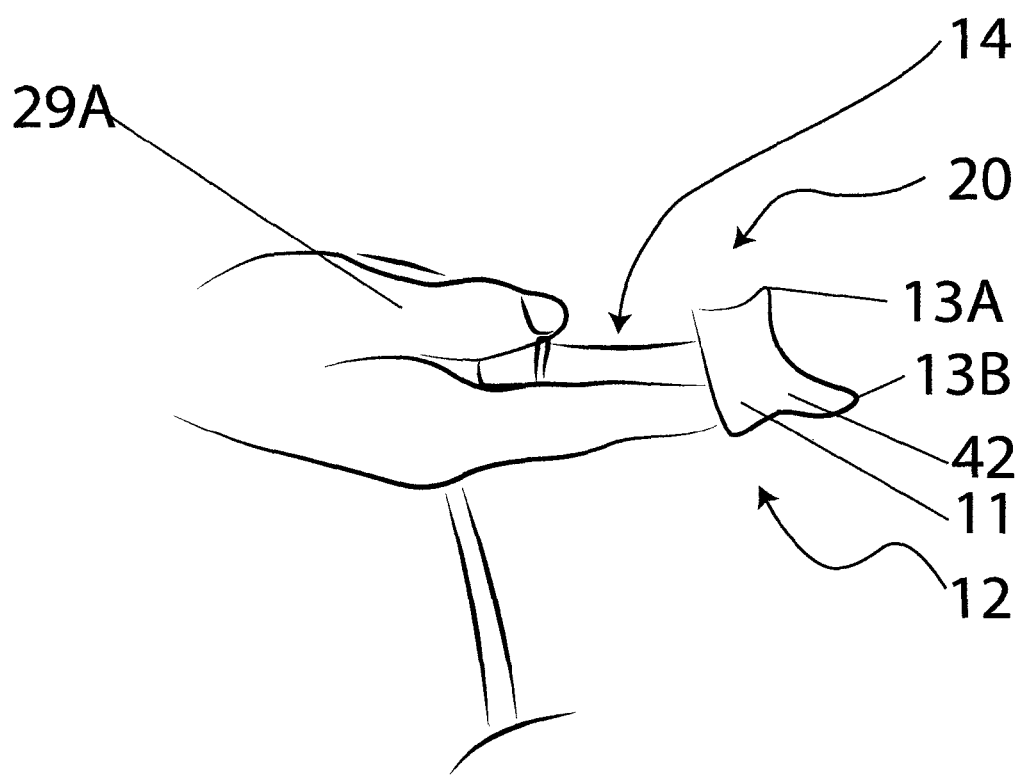
FIGS. 12A to 12F illustrate, in sequence, the process of connecting the female urinary device of FIG. 7 to the genitalia of a female.

In the following, the sequence of the activities of connecting and disconnecting the urinary device to the body of a treated female (78) is shown. The connecting activities are shown in a sequence of figures: FIG. 12A to and including FIG. 12F. The disconnecting activities are shown in a sequence of FIGS. 12D, 13A and 13B. The connecting and disconnecting activities, shown in FIG. 12A to and including 13B, show the use of the second embodiment of the urinary device (urinary device (20)). The identical procedure of activities connecting and disconnecting urinary device (20) to the body of a treated female (78) is used in connecting the other three embodiments of the urinary device ((10), (30) and (40)).

In the first stage of connecting, shown in FIG. 12A, urinary device (20) is held in an approximate horizontal position by the palm of the hand (29A) of the user/care giver and in close location to the genitalia (75). The backside portion (13B) of receiving receptacle vessel (11) of the urinary device is positioned in the direction of the floor. The receiving receptacle vessel (11) is part of the CUCC (12) and is partially "hidden" below the round skirt-like structure (42). When urinary device (20) is being connected, the user is typically in a lying position.

Figure 12B:
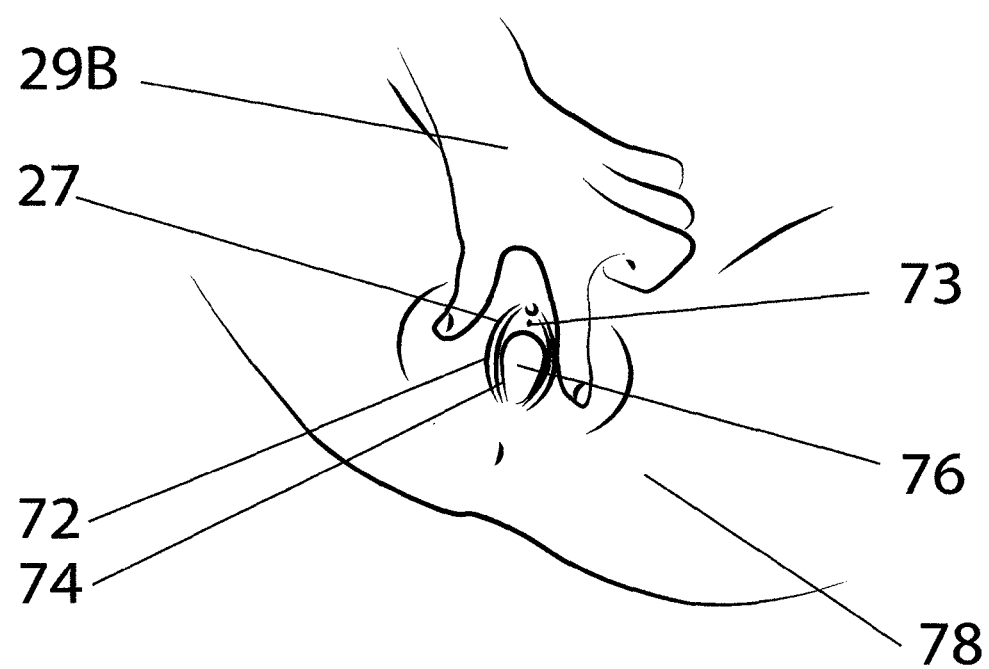

In the second stage, shown in FIG. 12B the user/caregiver, using her fingers, stretch-spreads the labia majora (72) and labia minora (74) and stretches the tissue around the UOSS (27) with her the fingers of her other hand (29B). The vagina orifice (76) and the urethral orifice (73) are now exposed.

Figure 12C:
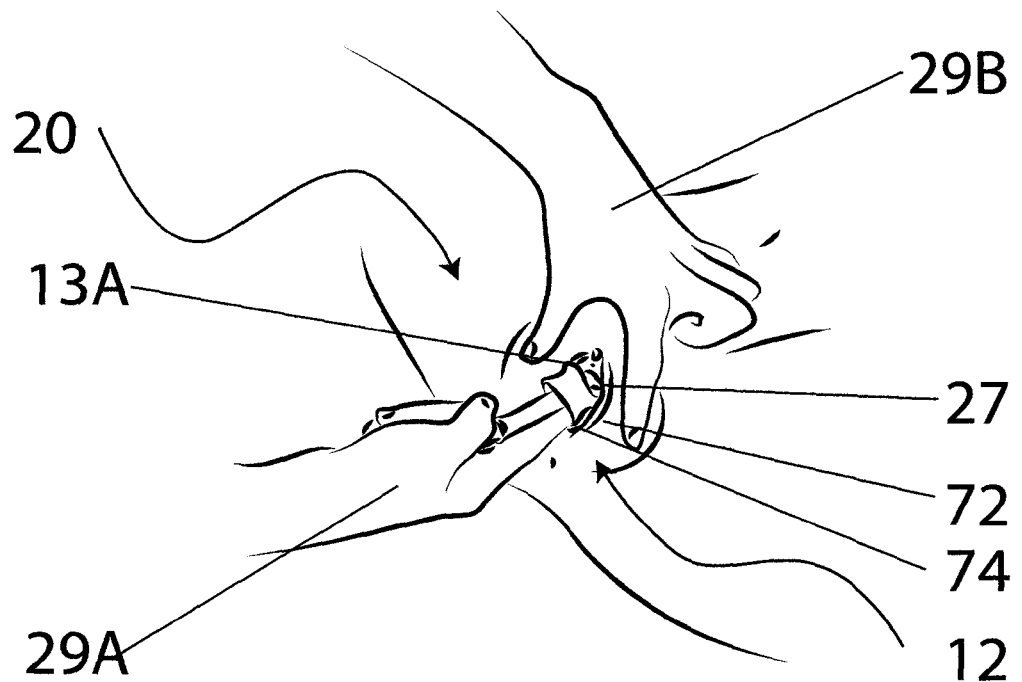

In the third stage, shown in FIG. 12C, urinary device (20) is placed in the space between the inner ward facing surfaces of the labia majora (72) and labia minora (74) and the UOSS (27). The backside portion (13B) of receptacle vessel (11) of CUCC (12) is inserted into the rim of the vagina orifice (76) in the rear direction of the user.

Figure 12D:
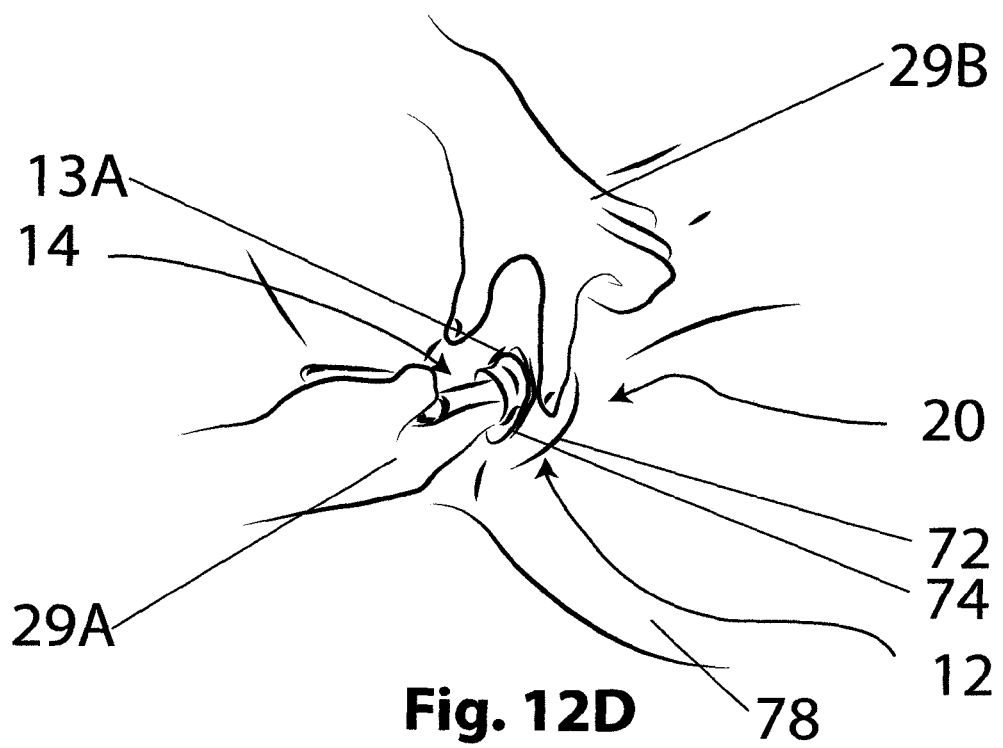

In the fourth stage, shown in FIG. 12D, the frontal portion (13A) of receiving receptacle vessel (11) is inserted into the converging end of the spread lips of the labia majora (72) labia minora (74) in the frontal direction of the user and CUCC (12) of urinary device (20) is pushed towards the body of the user. In the pushing, the smooth inner-surface (15) of the semi-rigid urine receiving receptacle (11) is pressed against the UOSS (27) and margin ring (18) is tightly pressed against the margins of the UOSS (27), securing a urine leak-proof sealing.

Figure 12E:

In the fifth stage, shown in FIG. 12E, after the inserting of CUCC (12) the stretched labia majora (72), labia minora (74) and UOSS (27) seek to return to their relaxed, un-stretched state. The user/care giver, using her fingers, assists in the closing of the spread labia majora (72) and labia minora (74) over CUCC (12). The user/care taker verifies and ensures the stable and tight connection of margin ring (18) to UOSS (27) and the connection of the outer walls of receiving receptacle vessel (11) to the inner sides of labia majora (72) and labia minora (74).

Figure 12F:

In the sixth stage, shown in FIG. 12F, urinary device (20) is stably connected to the genitalia of the user. The tube of UDDC (14) is shown protruding from the closed lips of the labia majora (72).

By inserting the backside portion (13B) of receptacle vessel (11) of CUCC (12) into the rim of the vagina orifice (76) (in stage three), CUCC (12) of urinary device (20) is guided to be placed over the urethral orifice and is in a stabilized configuration in the body of the user. In the following stage (stage four), by pressing the smooth inner-surface (15) of the semi-rigid urine receiving receptacle (11) against the UOSS (27) and margin ring (18) against the margins of the UOSS (27), an adhesion connection is formed via a "sticking phenomena." The "sticking phenomena" is formed in the intimate contact spots between the two compatible smooth surfaces. As the pressure is applied, more and more contact spots are established and the adhesion enhances as. The sticking is further enhanced if and when moisture from vaginal secretion or/and urine forms a film between the two smooth surfaces. When the labia majora and labia minora "close in" on the CUCC (12), as described in stage five, the mechanical pressure force exerted on the CUCC (12) contributes to maintaining the pressure of the receiving receptacle (11) against the UOSS and its margin (27) as well as adding in stabilizing urinary device (20) in place. The contact of the smooth inner surfaces of the labia majora and labia minora with the smooth external surface of receiving receptacle (11) join in (and also) form an adhesion connection in the form of a "sticking phenomena."

Reference is presently made to the disconnecting stages of urinary device (20) from the body of a female.

In the first stage, shown in FIG. 12D, the user/care giver opens-spreads the labia majora (72) and labia minora (74) widely. The spreading releases the "closing in" mechanical-force and helps releasing the adhesion force that connects the urinary device to the genitalia.

Figure 13A:
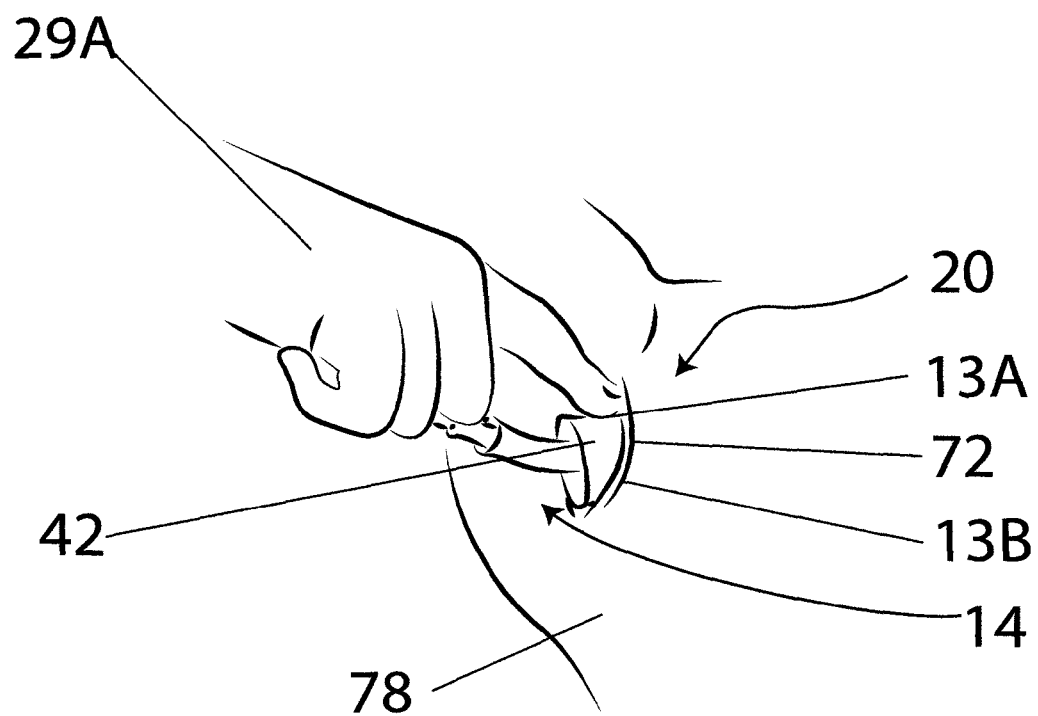
FIGS. 13A and 13B illustrate, in sequence, the process of disconnecting the female urinary device of FIG. 7 from the genitalia of a female.

In the second stage, shown in FIG. 13A, the receiving receptacle (11) of CUCC (12) is gently peeled off from its contact with the UOSS (27), starting from (13A) towards (13B), and removed from the body of the user.

Figure 13B:
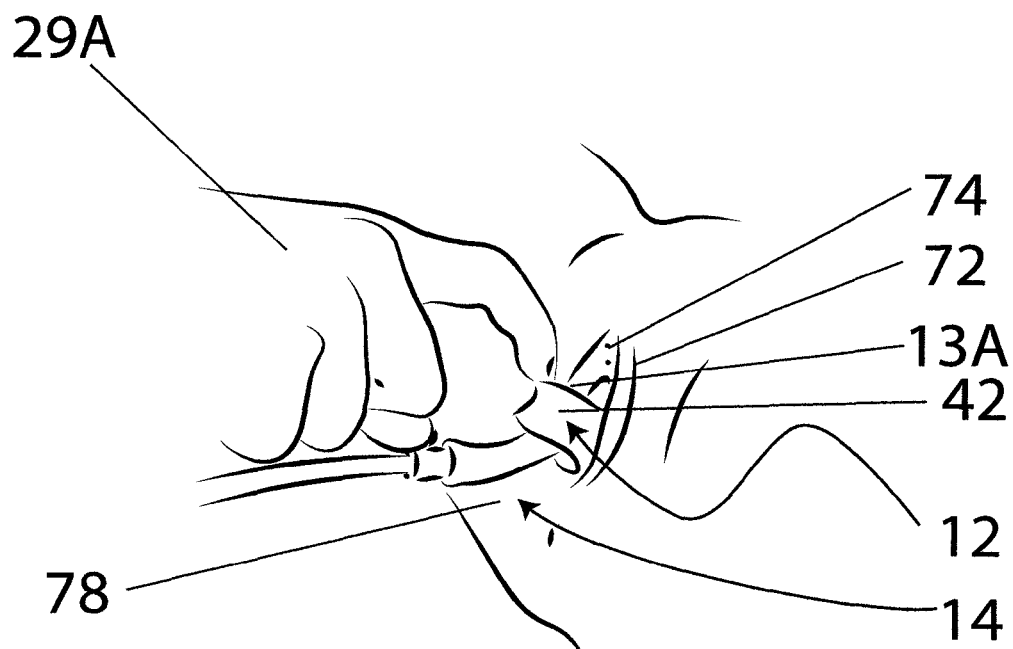

In the third stage, shown in FIG. 13B, urinary device (20) is completely peeled from the contact with the UOSS (27) and removed from the body of the user.

Figure 14:
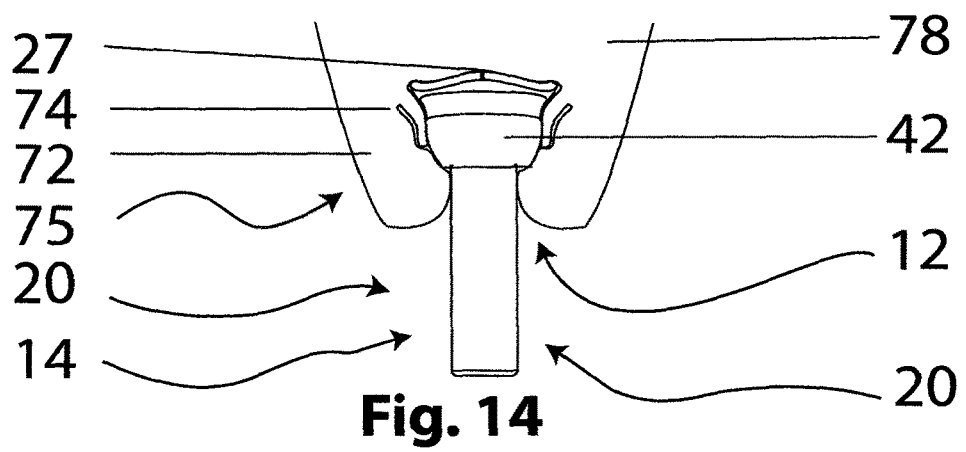
FIG. 14 illustrates a cross-section of the female urinary device of FIG. 7 when connected to the genitalia of a female.

FIG. 14 shows a crosscut illustration, as seen from above, of the urinary device (20), connected to the genitalia of a treated female (78). The illustration shows the adhesion connection of the urinary device (20) with the smooth urethral orifice surrounding skin (UOSS) (27) and the labia majora (72) and labia minora (74) connected by adhesion and "closed in" on the CUCC (12). The flexible, resilient and smooth surface skirt structure (42) is shown filling the space between h labia majora (72) and labia minora (74) and the UOSS (27).

Figure 15A:
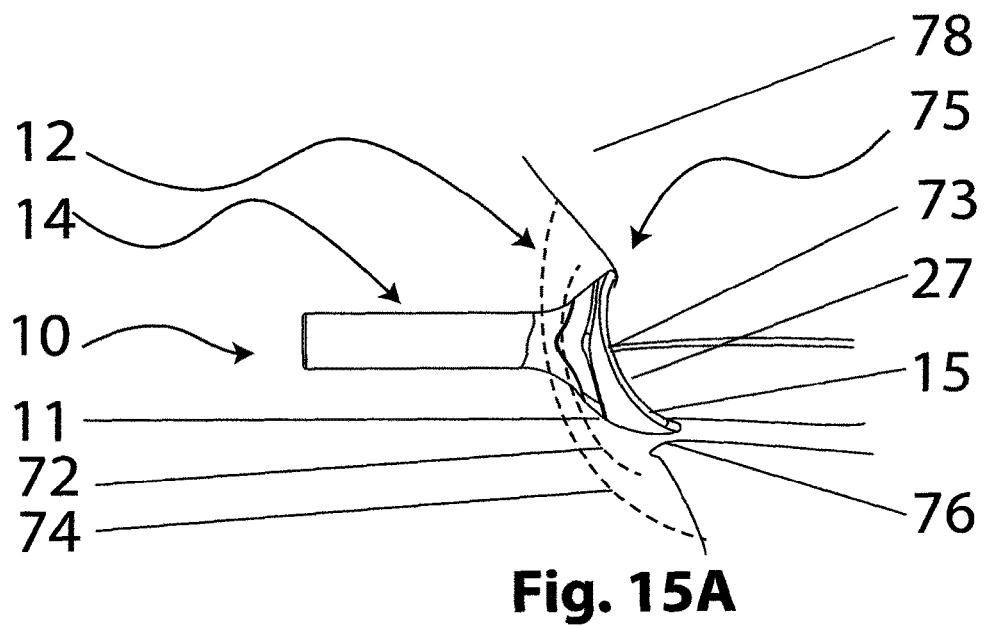
FIG. 15A illustrates a cross-section of the genitalia of a female when connected to the female urinary device of FIG. 7.
Figure 15B:
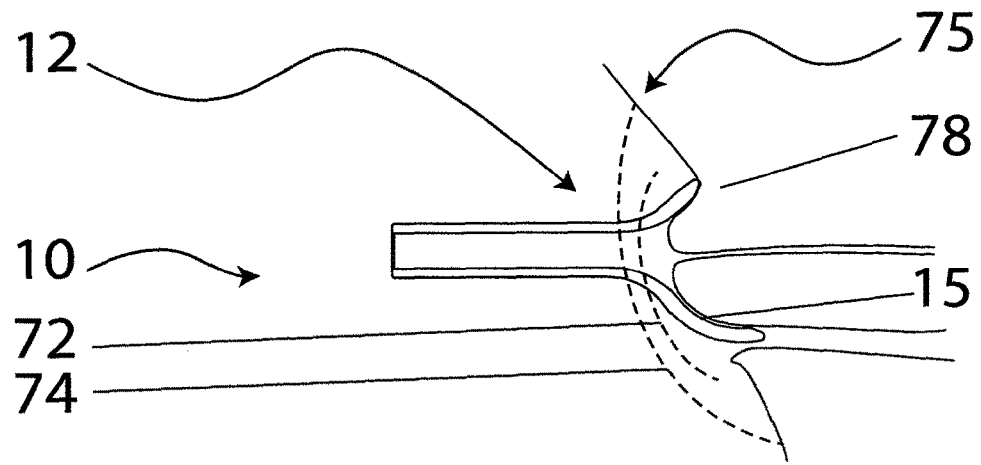
FIG. 15B illustrates a cross-section of the genitalia of a female and a cross-section of the urinary device, of FIG. 15A, connected to the genitalia.

FIG. 15A shows a crosscut illustration of a genitalia of a female shown with a connected (not-crosscut) urinary device (10), shown in FIG. 1. FIG. 15B is a crosscut illustration of the genitalia and the crosscut of a connected urinary device, shown in FIG. 15A. The figures illustrate the insertion of the urinary device (for all four embodiments described in the text) into the vaginal orifice (76) for stabilization and the adhesion connection of smooth inner and external surfaces (15) of urine receiving receptacle vessel (11) with the (UOSS) (27) and the labia majora (72) and labia minora (74) of a treated female (78) while enabling an open passage from the urethral orifice (73) and hole (16) leads to tube (17) of UDDC (14).

Figure 16:
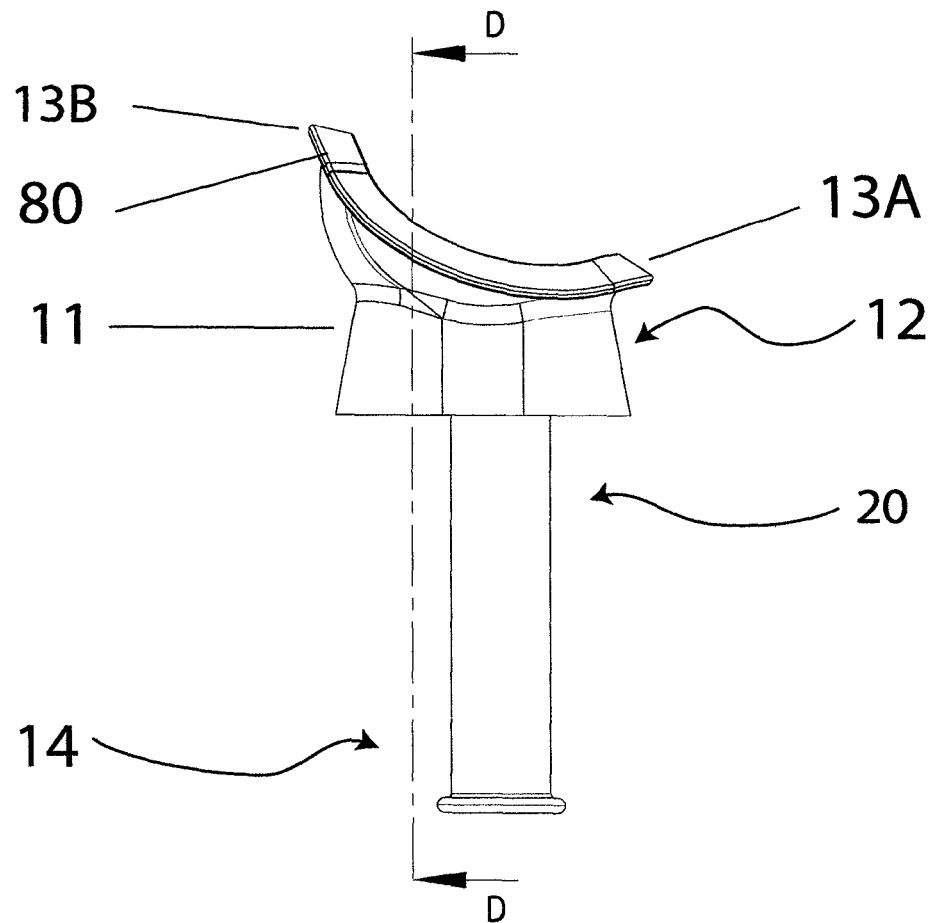
FIG. 16 illustrates a side view of the female urinary device of FIG. 7 that further includes a T-shaped structure surrounding the rim of the open urine collecting component of the female urinary device.
Figure 16A:
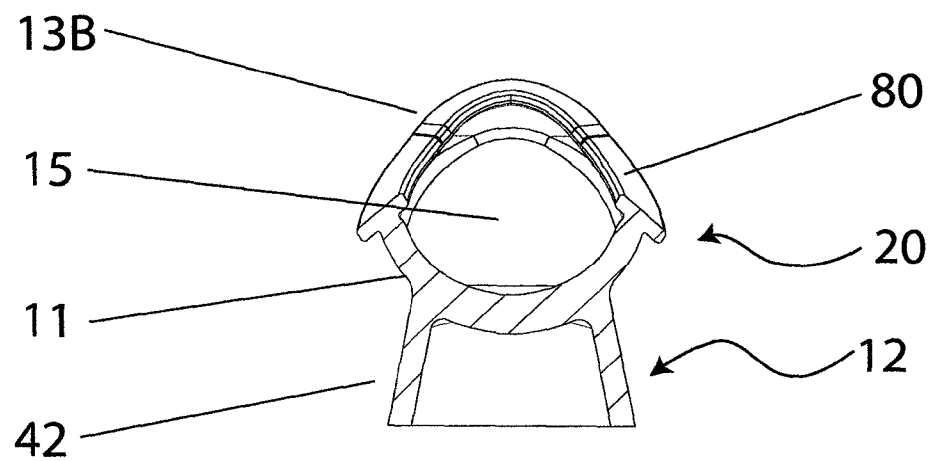
FIG. 16A illustrates a view along cross-section D-D shown in FIG. 16.

FIG. 16 shows an illustration seen from the side of urinary device (20), shown in FIG. 7, with a T-shaped configuration structure (80) surrounding the rim of the urine receiving receptacle vessel (11). The T-shaped configuration structure (80) replaces the smooth margin-ring (18) of urine receiving receptacle vessel (11), shown in FIG. 7 and FIG. 8. FIG. 16A is a crosscut illustration of section D-D shown in FIG. 16 as seen from the front of urinary device (20).

The T-shaped configuration structure (80) is a flat plate-structure perpendicularly connected to the rim edge of the urine receiving receptacle vessel (11) and serves to increase the contact surface area of the rim-ring- of urine receiving receptacle vessel (11), thus increasing the adhesion force between the urine receiving receptacle vessel (11) and the UOSS (27).

Although a few variations have been described in detail above, other modifications can be possible. For example, the logic flows depicted in the accompanying figures and described herein do not require the particular order shown, or sequential order, to achieve desirable results. For some implementations, the drawings shown are isometric illustrations of those implementations. For some alternate implementations, any change in proportionality is possible. Additional implementations may be within the scope of the following claims.

What is claimed is:

1. A urine collection device comprising:
    a urine collecting component (UCC) comprising a hollow funnel having a larger upper orifice and a smaller lower orifice, the hollow funnel tapering from the upper orifice to the lower orifice; and
    a urine discharging component (UDC) comprising a hollow tube adapted to communicate with the lower orifice of the UCC and provide a continuous duct for passage and discharge of urine from the UCC, wherein
    the UCC further comprises a margin ring that defines the upper orifice, the margin ring having a crescent shape characterized by a back side peak and a front side peak, the back side peak extending a first vertical distance from the lower orifice and the front side peak extending a second vertical distance from the lower orifice, the first vertical distance being greater than the second vertical distance, the UCC is adapted for insertion into the vulva of a female user, with the margin ring positioned internally within the labia minora and pressed against urethral orifice surrounding skin (UOSS), and the margin ring is formed from a semi-rigid, smooth surface viscoelastic material having a surface tension equivalent to or less than that of skin, with an upper surface of the margin ring adapted for contacting and adhering to the UOSS through an adhesion force between the contacting surfaces such that, upon the margin ring being pressed against the UOSS while the UOSS is in a moistened state and then releasing such pressing force, the margin ring will remain adhered to the UOSS without an adhesive.

2. The urine collection device of claim 1, wherein an inner surface of the hollow funnel is formed from a semi-rigid, smooth surface viscoelastic material having a surface tension equivalent to or less than that of skin such that, upon the inner surface of the hollow funnel being pressed against the UOSS while the UOSS is in a moistened state and then releasing such pressing force, the inner surface of the hollow funnel will remain adhered to the UOSS without an adhesive.

3. The urine collection device of claim 1, wherein an outer surface of the UCC is formed from a semi-rigid, smooth surface viscoelastic material having a surface tension equivalent to or less than that of skin such that, upon the UCC being pressed against the labia minora and/or the labia majora while the labia minora and/or the labia majora is in a moistened state and then releasing such pressing force, the outer surface of the UCC will remain adhered to an inner wall of the labia minora and/or the labia majora without an adhesive.

4. The urine collection device of claim 1, wherein the UCC is dimensioned such that, upon being inserted within the labia majora and the labia minora, the UCC is further retained in position by exertion of a closing-in force on the UCC by inner walls of the labia majora and/or inner walls of the labia minora.

5. The urine collection device of claim 1, wherein the back side peak of the margin ring is adapted for insertion into the vaginal orifice for positioning the upper orifice of the margin ring to circumscribe the urethral orifice.

6. The urine collection device of claim 1, wherein the viscoelastic material that adheres to the internal skin of the vulva is a biocompatible silicone based material or a biocompatible polytetrafluoroethylene based material.

7. The urine collection device of claim 1, wherein the UCC and the UDC are adapted to retain their spatial configurations relative to one another upon the UCC being adhered to moistened internal skin of the vulva.

8. The urine collection device of claim 1, wherein the UCC and the UDC are a single entity structure.

9. The urine collection device of claim 1, wherein the margin ring of the UCC comprises a substantially horizontal flat contact surface for pressing against the UOSS, the flat contact surface being substantially perpendicular to a substantially vertical upper edge of an outer wall of the hollow funnel.

10. The urine collection device of claim 1, wherein the urine collection device excludes support structures adapted for applying an external force for keeping the margin ring pressed against the UOSS.

11. The urine collection device of claim 1, further comprising:

a flexible and resilient skirt connected to and surrounding the UCC, the skirt being connected to an approximate middle region of an outer surface of the UCC, the outer surface of the UCC tapering between the larger upper orifice and the smaller lower orifice of the hollow funnel, the skirt having an oval shape and tapering from a smaller circumference at a point where the skirt is connected to the UCC to a larger circumference at a lower free end of the skirt.

12. The urine collection device of claim 11, wherein the skirt is formed from a semi-rigid, smooth surface viscoelastic material having a surface tension equivalent to or less than that of skin such that, upon the skirt being pressed against the internal skin while the internal skin is in a moistened state and then releasing such pressing force, the skirt will remain adhered to the internal skin without an adhesive.

13. The urine collection device of claim 1, wherein the UCC is configured such that, upon insertion into the vulva of a female user, the back side peak of the margin ring is positioned to abut an anterior wall of the vagina.

14. A method of using the urine collection device of claim 1, comprising:

inserting the UCC into the vulva of a female user, with the margin ring positioned within the labia minora and the upper orifice of the margin ring circumscribing the urethral orifice; and pressing the margin ring against the UOSS, while the UOSS is in a moistened state, so as to generate an adhesion force between the margin ring and the UOSS, such that upon releasing the pressing force the margin ring remains adhered to the UOSS without an adhesive.

15. The method according to claim 14, further comprising:

before inserting the UCC into the vulva, applying a biocompatible wetting-agent to the margin ring of the UCC and/or an internal skin surface of the vulva.

16. The method according to claim 14, wherein inserting the UCC into the vulva comprises inserting the back side peak of the margin ring into the vaginal orifice and positioning the front side peak of the margin ring within the anterior convergence of the labia minora.

17. The method according to claim 14, wherein the urine collection device excludes support structures adapted for applying an external force for keeping the margin ring pressed against the UOSS.

18. The method according to claim 14, wherein inserting the UCC into the vulva comprises inserting the back side peak of the margin ring to abut an anterior wall of the vagina.

19. A urine collection device comprising:

a urine collecting component (UCC) comprising a hollow funnel having a larger upper orifice and a smaller lower orifice, the hollow funnel tapering from the upper orifice to the lower orifice; and a urine discharging component (UDC) comprising a hollow tube adapted to communicate with the lower orifice of the UCC and provide a continuous duct for passage and discharge of urine from the UCC, wherein the UCC further comprises a margin ring that defines the upper orifice, the margin ring having a crescent shape characterized by a back side peak and a front side peak, the back side peak extending a first vertical distance from the lower orifice and the front side peak extending a second vertical distance from the lower orifice, the first vertical distance being greater than the second vertical distance, the UCC is adapted for insertion into the vulva of a female user, with the margin ring positioned internally within the labia minora and pressed against urethral orifice surrounding skin (UOSS), the margin ring is formed from a viscoelastic material with an upper surface of the margin ring adapted for contacting and adhering to the UOSS through an adhesion force between the contacting surfaces such that, upon the margin ring being pressed against the UOSS while the UOSS is in a moistened state and then releasing such pressing force, the margin ring will remain adhered to the UOSS without an adhesive, and the urine collection device further comprises a flexible and resilient skirt connected to and surrounding the UCC, the skirt being connected to an approximate middle region of an outer surface of the UCC, the outer surface of the UCC tapering between the larger upper orifice and the smaller lower orifice of the hollow funnel, the skirt having an oval shape and tapering from a smaller circumference at a point where the skirt is connected to the UCC to a larger circumference at a lower free end of the skirt.

20. A urine collection device comprising:

a urine collecting component (UCC) comprising a hollow funnel having a larger upper orifice and a smaller lower orifice, the hollow funnel tapering from the upper orifice to the lower orifice; and a urine discharging component (UDC) comprising a hollow tube adapted to communicate with the lower orifice of the UCC and provide a continuous duct for passage and discharge of urine from the UCC, wherein the UCC further comprises a margin ring that defines the upper orifice, the margin ring having a crescent shape characterized by a back side peak and a front side peak, the back side peak extending a first vertical distance from the lower orifice and the front side peak extending a second vertical distance from the lower orifice, the first vertical distance being greater than the second vertical distance, the UCC is adapted for insertion into the vulva of a female user, with the margin ring positioned internally within the labia minora and pressed against urethral orifice surrounding skin (UOSS), the margin ring is formed from a viscoelastic material with an upper surface of the margin ring adapted for contacting and adhering to the UOSS through an adhesion force between the contacting surfaces such that, upon the margin ring being pressed against the UOSS while the UOSS is in a moistened state and then releasing such pressing force, the margin ring will remain adhered to the UOSS without an adhesive, and the UCC is configured such that, upon insertion into the vulva of a female user, the back side peak of the margin ring is positioned to abut an anterior wall of the vagina.

* * * * *